US009284245B2

(12) United States Patent
Lee et al.

(10) Patent No.: US 9,284,245 B2
(45) Date of Patent: Mar. 15, 2016

(54) MONOMER FOR HARDMASK COMPOSITION AND HARDMASK COMPOSITION INCLUDING THE MONOMER AND METHOD OF FORMING PATTERNS USING THE HARDMASK COMPOSITION

(71) Applicants: Sung-Jae Lee, Uiwang-si (KR); Hwan-Sung Cheon, Uiwang-si (KR); Youn-Jin Cho, Uiwang-si (KR); Chul-Ho Lee, Uiwang-si (KR); Chung-Heon Lee, Uiwang-si (KR)

(72) Inventors: Sung-Jae Lee, Uiwang-si (KR); Hwan-Sung Cheon, Uiwang-si (KR); Youn-Jin Cho, Uiwang-si (KR); Chul-Ho Lee, Uiwang-si (KR); Chung-Heon Lee, Uiwang-si (KR)

(73) Assignee: CHEIL INDUSTRIES, INC., Gumi-si, Kyeongsangbuk-do (KR)

( * ) Notice: Subject to any disclaimer, the term of this patent is extended or adjusted under 35 U.S.C. 154(b) by 63 days.

(21) Appl. No.: 14/083,598

(22) Filed: Nov. 19, 2013

(65) Prior Publication Data

US 2014/0186777 A1   Jul. 3, 2014

(30) Foreign Application Priority Data

Dec. 27, 2012  (KR) .................. 10-2012-0155330

(51) Int. Cl.
| | | |
|---|---|---|
| *C07C 43/23* | (2006.01) | |
| *G03F 7/09* | (2006.01) | |
| *G03F 7/20* | (2006.01) | |
| *C07C 33/26* | (2006.01) | |
| *G03F 7/075* | (2006.01) | |
| *G03F 7/40* | (2006.01) | |

(52) U.S. Cl.
CPC ................. *C07C 33/26* (2013.01); *C07C 43/23* (2013.01); *G03F 7/0752* (2013.01); *G03F 7/09* (2013.01); *G03F 7/40* (2013.01)

(58) Field of Classification Search
CPC ........ C07C 39/04; C07C 39/12; C07C 39/16; C07C 32/26; C07C 43/23; G03F 7/09; G03F 7/095; G03F 7/11; G03F 7/20
See application file for complete search history.

(56) References Cited

U.S. PATENT DOCUMENTS

| | | | |
|---|---|---|---|
| 2005/0255651 A1* | 11/2005 | Qian et al. .................... 438/257 |
| 2010/0021830 A1 | 1/2010 | Kim et al. | |
| 2011/0155944 A1 | 6/2011 | Cho et al. | |
| 2012/0153511 A1 | 6/2012 | Song et al. | |

FOREIGN PATENT DOCUMENTS

| | | |
|---|---|---|
| CN | 101470352 A | 7/2009 |
| CN | 102566281 A | 7/2012 |
| KR | 10-2009-0068444 A | 6/2009 |
| KR | 10-2011-0079201 A | 7/2011 |
| KR | 10-2012-0067602 A | 6/2012 |
| KR | 10-2012-0068379 A | 6/2012 |
| WO | WO 2012/005418 A1 | 1/2012 |

OTHER PUBLICATIONS

Search Report dated Jan. 28, 2015 in corresponding Taiwanese Patent Application No. 102126270.
Chinese Search Report for 201310300799.1 dated Mar. 13, 2015; Lee, et al.

* cited by examiner

*Primary Examiner* — Anca Eoff
(74) *Attorney, Agent, or Firm* — Lee & Morse, P.C.

(57) ABSTRACT

A monomer for a hardmask composition represented by the following Chemical Formula 1,

[Chemical Formula 1]

$$\left(X_1-A_1-L_1'\underset{}{\overset{OH}{\bigg\langle}}A_0-L_1\right)_m \left(L_2-A_0\underset{}{\overset{OH}{\bigg\langle}}L_2'-A_2-X_2\right)_n$$

16 Claims, 1 Drawing Sheet

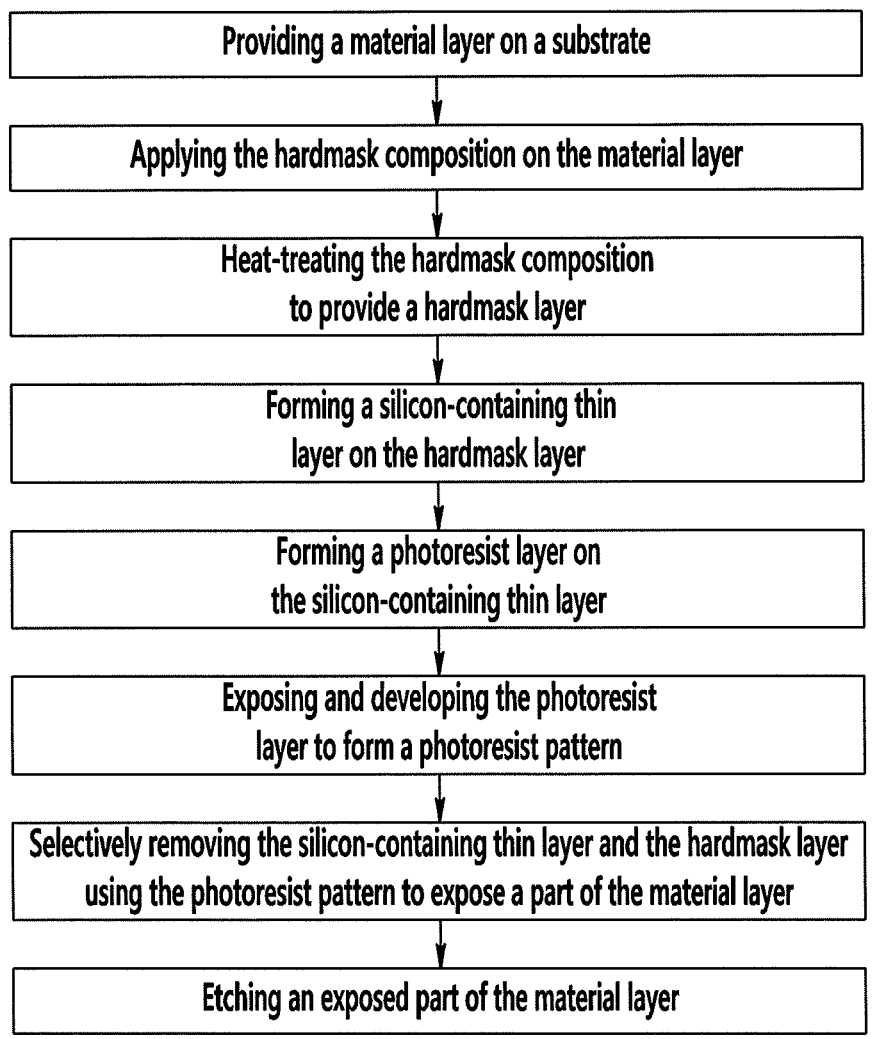

MONOMER FOR HARDMASK COMPOSITION AND HARDMASK COMPOSITION INCLUDING THE MONOMER AND METHOD OF FORMING PATTERNS USING THE HARDMASK COMPOSITION

CROSS-REFERENCE TO RELATED APPLICATION

Korean Patent Application No. 10-2012-0155330, filed on Dec. 27, 2012, in the Korean Intellectual Property Office, and entitled: "Monomer For Hardmask Composition and Hardmask Composition Including the Monomer and Method of Forming Patterns Using the Hardmask Composition," is incorporated by reference herein in its entirety.

BACKGROUND

1. Field

Embodiments relate to a monomer for a hardmask composition, a hardmask composition including the monomer, and a method of forming patterns using the hardmask composition.

2. Description of the Related Art

The semiconductor industry has developed an ultra-fine technique for providing a pattern of several to several tens nanometer size. Such an ultrafine technique benefits from effective lithographic techniques.

A typical lithographic technique includes providing a material layer on a semiconductor substrate, coating a photoresist layer thereon, exposing and developing the same to provide a photoresist pattern, and etching the material layer using the photoresist pattern as a mask.

According to small-sizing of the pattern to be formed, it may be difficult to provide a fine pattern having a desirable profile by only above-mentioned typical lithographic technique. Accordingly, a layer, called a hardmask layer, may be formed between the material layer and the photoresist layer to provide a fine pattern.

SUMMARY

Embodiments are directed to a monomer for a hardmask composition, the monomer being represented by the following Chemical Formula 1:

[Chemical Formula 1]

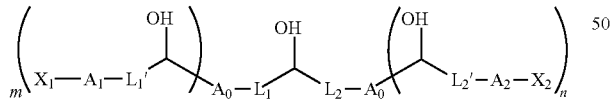

In the above Chemical Formula 1, $A_0$ may be a substituted or unsubstituted polycyclic aromatic group, $A_1$ and $A_2$ may each independently be a substituted or unsubstituted C6 to C20 aromatic group, $L_1, L_1', L_2$ and $L_2'$ may each independently be a single bond or a substituted or unsubstituted C1 to C6 alkylene group, $X_1$ and $X_2$ may each independently be hydrogen, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, and m and n may each independently be integers of 0 to 6, provided that m and n are not 0 simultaneously.

The $A_0$ may be selected from the following Group 1:

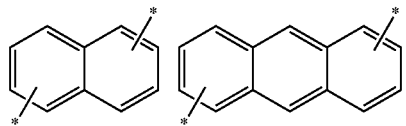

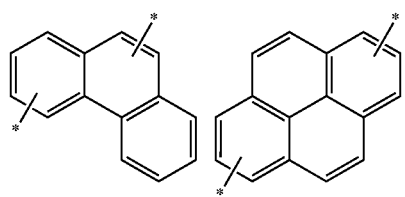

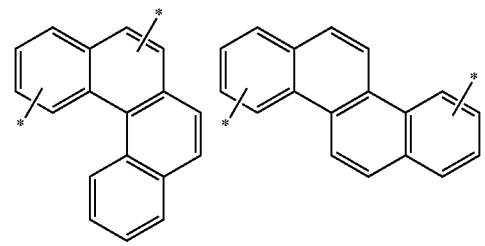

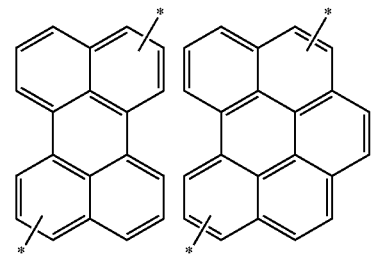

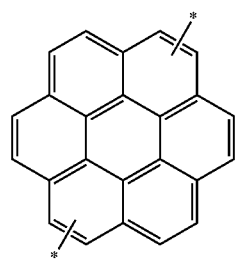

The $A_1$ and $A_2$ may each independently be a substituted or unsubstituted benzyl group, a substituted or unsubstituted naphthyl group, or a substituted or unsubstituted biphenyl group.

The monomer may be represented by one of the following Chemical Formulae 1-1, 1-2, 1-3, 1-4, 1-5, or 1-6:

[Chemical Formula 1-1]
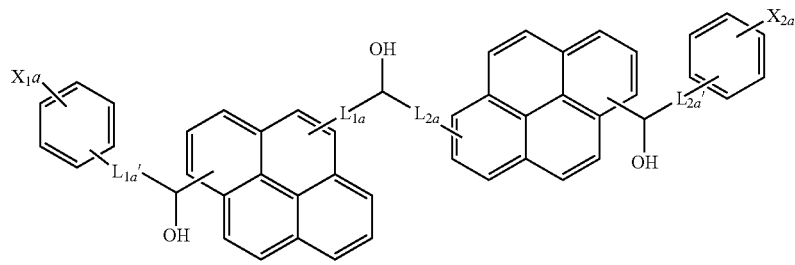
[Chemical Formula 1-2]
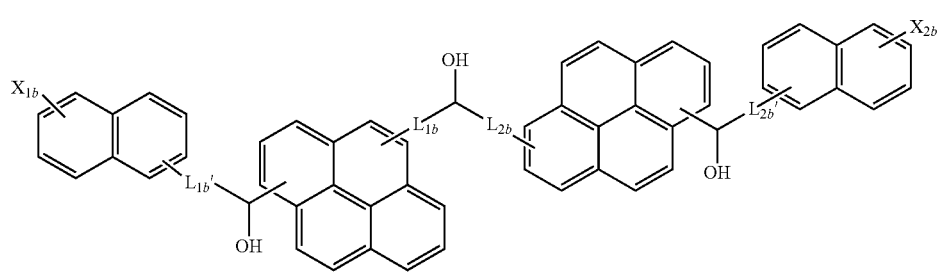
[Chemical Formula 1-3]
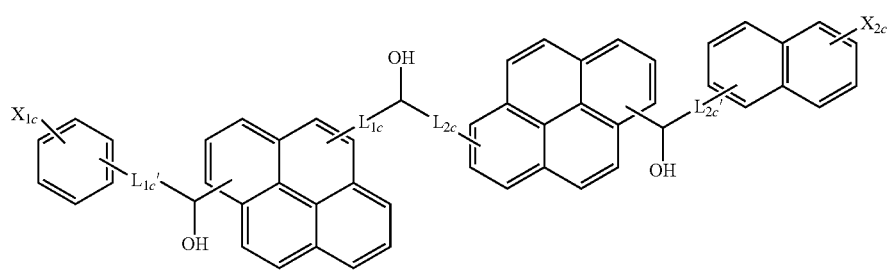
[Chemical Formula 1-4]
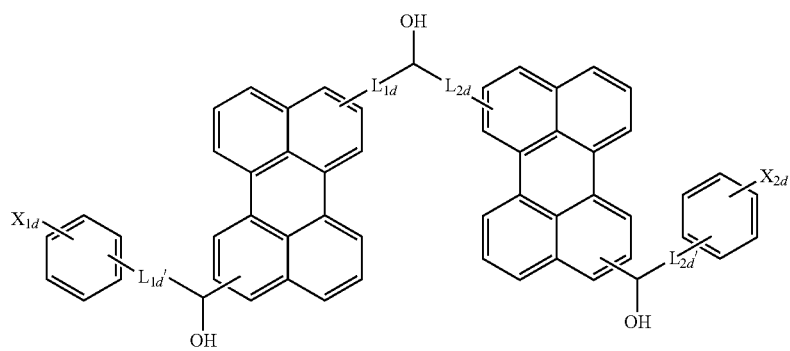
[Chemical Formula 1-5]
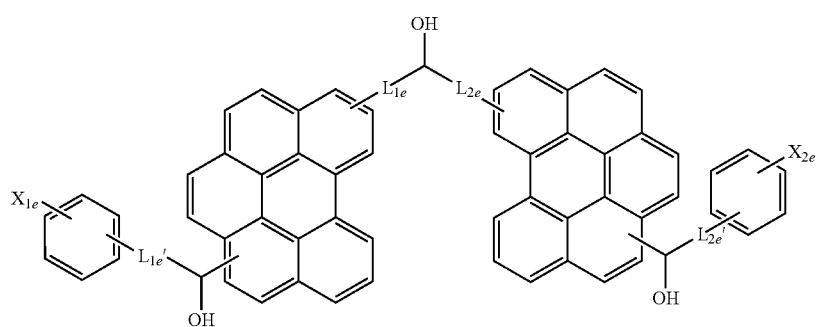

[Chemical Formula 1-6]

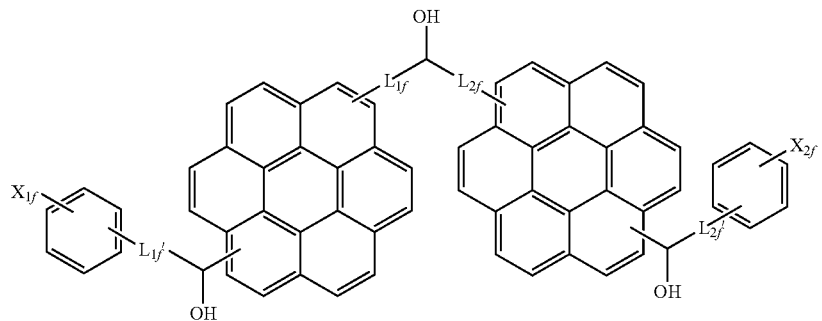

In the Chemical Formulae 1-1, 1-2, 1-3, 1-4, 1-5, and 1-6, $L_{1a}$, $L_{1b}$, $L_{1c}$, $L_{1d}$, $L_{1e}$, $L_{1f}$, $L_{2a}$, $L_{2b}$, $L_{2c}$, $L_{2d}$, $L_{2e}$, $L_{2f}$, $L_{1a}'$, $L_{1b}'$, $L_{1c}'$, $L_{1d}'$, $L_{1e}'$, $L_{1f}'$, $L_{2a}'$, $L_{2b}'$, $L_{2c}'$, $L_{2d}'$, $L_{2e}'$, and $L_{2f}'$ may each independently be a single bond or a substituted or unsubstituted C1 to C6 alkylene group, $X_{1a}$, $X_{1b}$, $X_{1c}$, $X_{1d}$, $X_{1e}$, $X_{1f}$, $X_{2a}$, $X_{2b}$, $X_{2c}$, $X_{2d}$, $X_{2e}$, and $X_{2f}$ may each independently be hydrogen, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, and linking positions of each ring are not particularly limited.

The monomer may be represented by one of the following Chemical Formulae 1aa, 1bb, 1ee, 1dd, 1ee, 1ff, or 1gg:

[Chemical Formula 1aa]

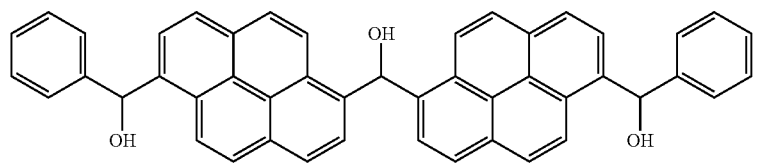

[Chemical Formula 1bb]

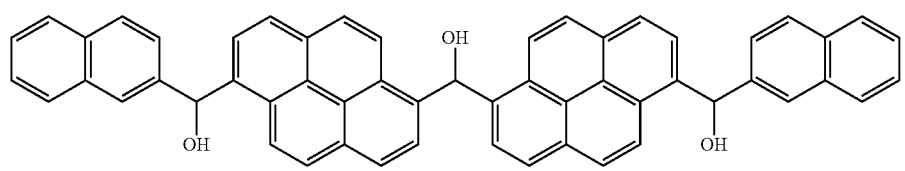

[Chemical Formula 1cc]

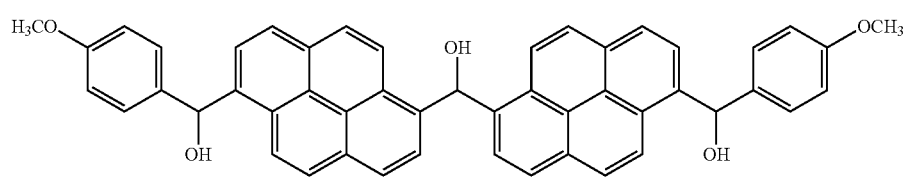

[Chemical Formula 1dd]

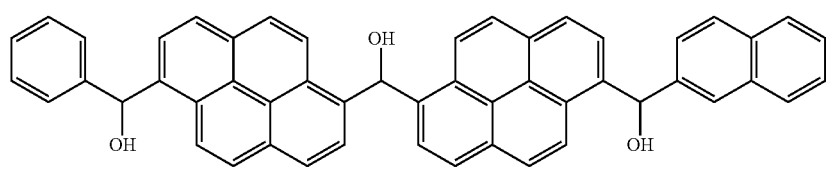

-continued

[Chemical Formula 1ee]

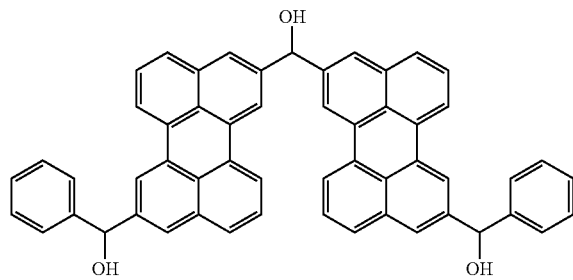

[Chemical Formula 1ff]

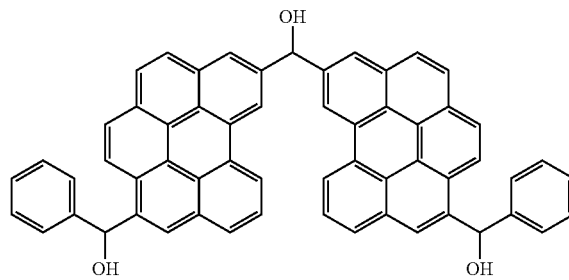

[Chemical Formula 1gg]

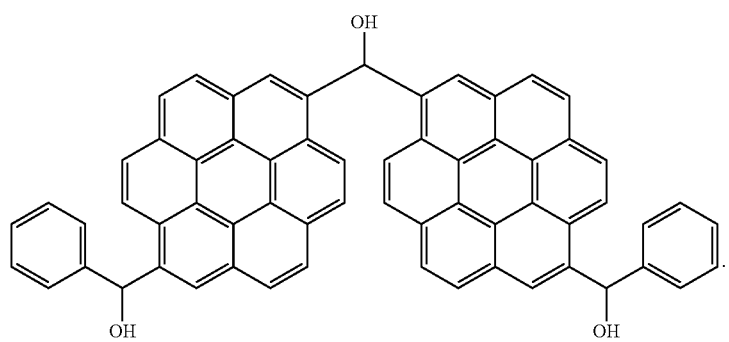

The monomer may have a molecular weight of about 500 to about 5,000.

Embodiments are also directed to a hardmask composition, including the monomer according to an embodiment, and a solvent.

The monomer may be included in an amount of about 1 to about 50 wt % based on a total amount of the hardmask composition.

Embodiments are also directed to a method of forming a pattern, the method including providing a material layer on a substrate, applying the hardmask composition as claimed in claim 7 on the material layer, heat-treating the hardmask composition to provide a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer using the photoresist pattern to expose a part of the material layer, and etching an exposed part of the material layer.

The hardmask composition may be applied using a spin-on coating method.

The hardmask layer may be formed by heat-treating the hardmask composition at about 100° C. to about 500° C.

BRIEF DESCRIPTION OF THE DRAWINGS

Features will become apparent to those of skill in the art by describing in detail example embodiments with reference to the attached drawings in which:

FIG. 1 illustrates a flow chart of a method of forming a pattern according to an embodiment.

DETAILED DESCRIPTION

Example embodiments will now be described more fully hereinafter; however, they may be embodied in different forms and should not be construed as limited to the embodiments set forth herein. Rather, these embodiments are provided so that this disclosure will be thorough and complete, and will fully convey exemplary implementations to those skilled in the art. Like reference numerals refer to like elements throughout.

As used herein, when a definition is not otherwise provided, the term 'substituted' refers to one substituted with at least a substituent selected from a halogen (F, Cl, Br, or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C2 to C20 alkenyl group, a C2 to C20 alkynyl group, a C6 to C30 aryl group, a C7 to C30 arylalkyl group, a C1 to C4 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C30 heterocycloalkyl group, and a combination thereof, instead of hydrogen of a compound.

As used herein, when a definition is not otherwise provided, the prefix "hetero" refers to one including 1 to 3 heteroatoms selected from N, O, S, and P.

Hereinafter, a monomer for a hardmask composition according to an example embodiment is described.

The monomer for a hardmask composition according to the present example embodiment may be represented by the following Chemical Formula 1.

[Chemical Formula 1]

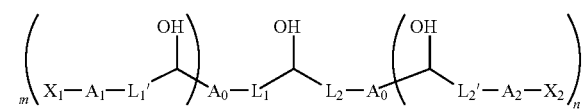

According to the present example embodiment, in the above Chemical Formula 1, $A_0$ is a substituted or unsubstituted polycyclic aromatic group, $A_1$ and $A_2$ are each independently a substituted or unsubstituted C6 to C20 aromatic group, $L_1$, $L_1'$, $L_2$ and $L_2'$ are each independently a single bond or a substituted or unsubstituted C1 to C6 alkylene group, $X_1$ and $X_2$ are each independently hydrogen, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, and m and n are independently integers of 0 to 6, provided that m and n are not 0 simultaneously.

In the above Chemical Formula 1, a substituent linked to $A_0, A_1$, and $A_2$ is not limited to specific rings of the $A_0, A_1$, and $A_2$ but may substitute hydrogen at any the rings of the $A_0, A_1$, and $A_2$.

In an implementation, the monomer has polycyclic aromatic groups at both sides of the hydroxyl group of a core.

The monomer having the aforementioned structure may have a rigid characteristic and may provide excellent resistance in a short wavelength region, e.g., less than or equal to about 248 nm.

The polycyclic aromatic group may be selected from the following Group 1.

[Group 1]

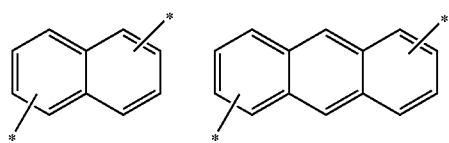

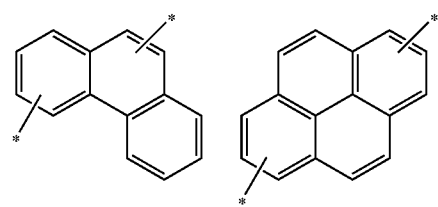

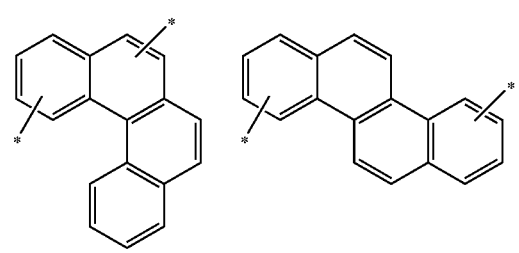

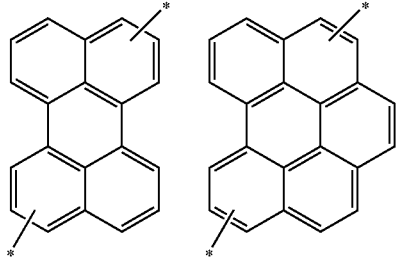

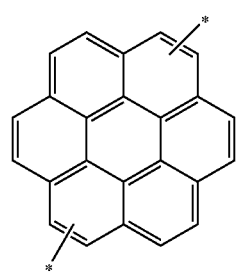

According to the present example embodiment, the monomer has a hydroxyl group in a core and has a hydroxyl group for a substituent at both sides of the core. The monomer may amplify cross-linking due to a condensation reaction that the hydroxyl groups may carry out, and excellent cross-linking characteristics may be provided. Accordingly, the monomer may be cross-linked into a polymer in a very short time even when heat-treated at a relatively low temperature, and may help provide excellent mechanical characteristics, heat resistance, chemical resistance, and etch resistance characteristics for a hardmask layer. In addition, the monomer includes a plurality of hydroxy groups for a substituent and may provide high dissolution in a solvent. The monomer may be prepared into a solution and be used in a spin-on coating method to form a hardmask layer. Further, the monomer according to the present example embodiment has a substituted or unsubstituted aromatic cyclic group for a substituent and may provide excellent etch resistance.

In the present example embodiment, $A_1$ and $A_2$ of the above Chemical Formula 1 are each independently a substituted or unsubstituted C6 to C20 aromatic group, an aromatic cyclic group.

In example embodiments, the aromatic cyclic group of the substituent may each independently be a substituted or unsubstituted benzyl group, a substituted or unsubstituted naphthyl group, or a substituted or unsubstituted biphenyl group.

An aromatic cyclic group of the substituent may include a hydroxy group, which may help improve etch resistance and dissolution.

The monomer may be represented by, e.g., one of the following Chemical Formulae 1-1, 1-2, 1-3, 1-4, 1-5, or 1-6.

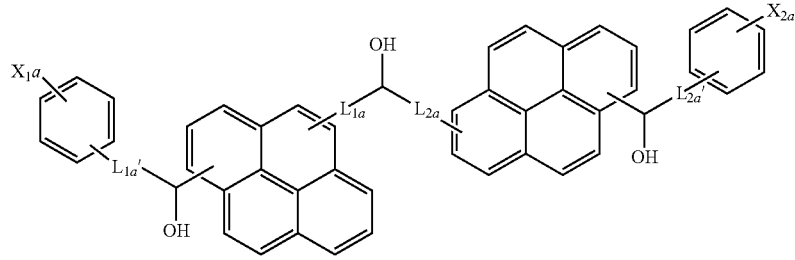
[Chemical Formula 1-1]
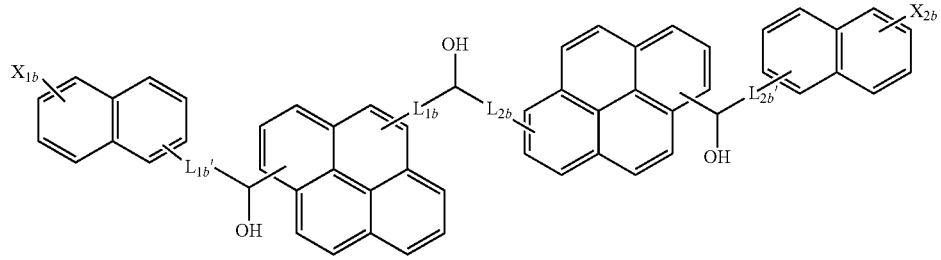
[Chemical Formula 1-2]
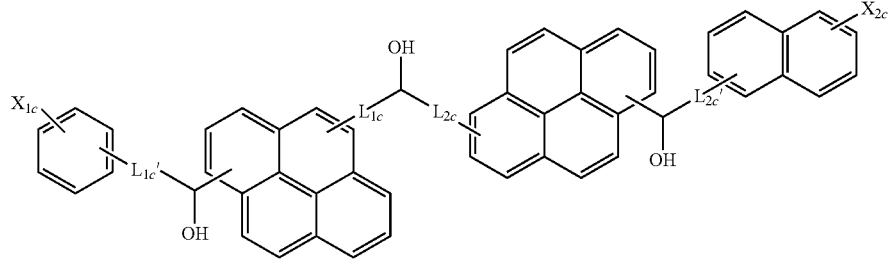
[Chemical Formula 1-3]
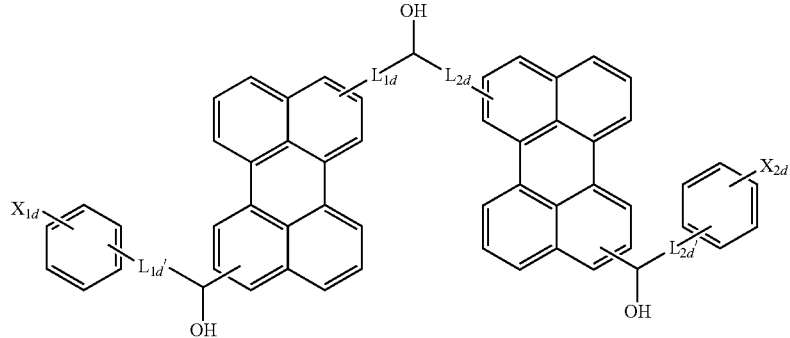
[Chemical Formula 1-4]
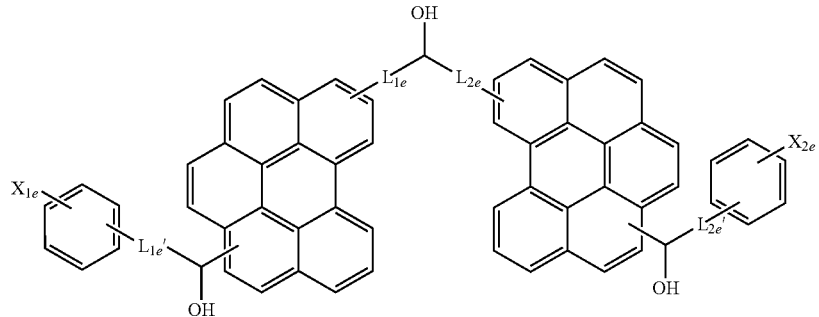
[Chemical Formula 1-5]

-continued

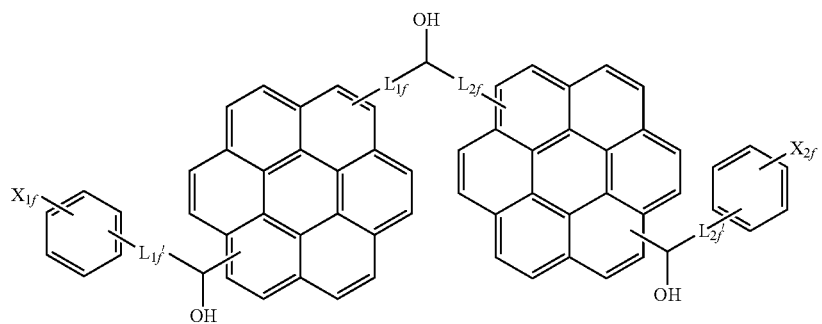

[Chemical Formula 1-6]

According to an example embodiment, in the Chemical Formulae 1-1, 1-2, 1-3, 1-4, 1-5, and 1-6, $L_{1a}$, $L_{1b}$, $L_{1c}$, $L_{1d}$, $L_{1e}$, $L_{1f}$, $L_{2a}$, $L_{2b}$, $L_{2c}$, $L_{2d}$, $L_{2e}$, $L_{2f}$, $L_{1a}'$, $L_{1b}'$, $L_{1c}'$, $L_{1d}'$, $L_{1e}'$, $L_{1f}'$, $L_{2a}'$, $L_{2b}'$, $L_{2c}'$, $L_{2d}'$, $L_{2e}'$, and $L_{2f}'$ are each independently a single bond or a substituted or unsubstituted C1 to C6 alkylene group, and $X_{1a}$, $X_{1b}$, $X_{1c}$, $X_{1d}$, $X_{1e}$, $X_{1f}$, $X_{2a}$, $X_{2b}$, $X_{2c}$, $X_{2d}$, $X_{2e}$, and $X_{2f}$ are each independently hydrogen, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group.

In the Chemical Formulae 1-1, 1-2, 1-3, 1-4, 1-5, and 1-6, linking positions of each ring are not particularly limited.

The monomer may be represented by, e.g., one of the following Chemical Formulae 1aa, 1bb, 1cc, 1dd, 1ee, 1ff, or 1gg.

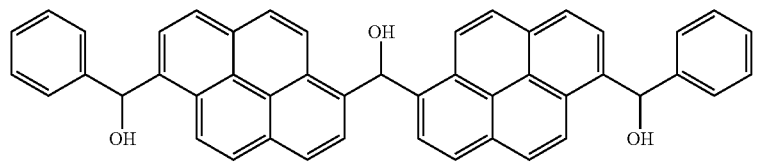

[Chemical Formula 1aa]

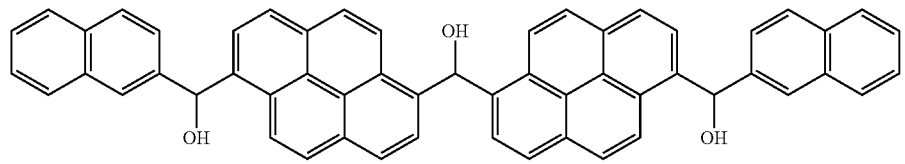

[Chemical Formula 1bb]

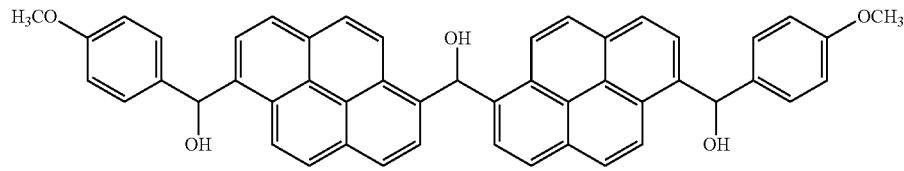

[Chemical Formula 1cc]

[Chemical Formula 1dd]

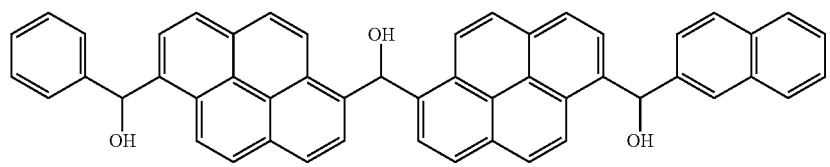

[Chemical Formula 1ee]

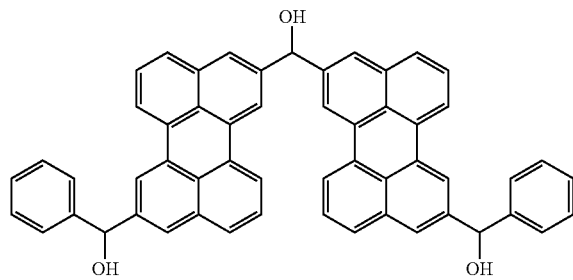

[Chemical Formula 1ff]

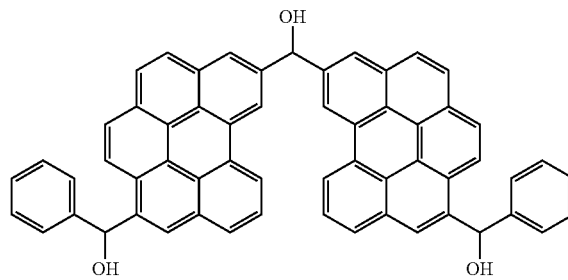

[Chemical Formula 1gg]

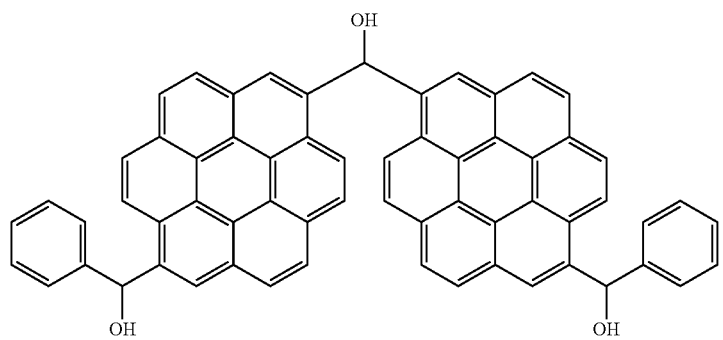

The monomer for a hardmask composition according to an example embodiment may have a molecular weight of about 500 to about 5,000. When the monomer has a molecular weight within the above range, solubility of the monomer having a high carbon content for a solvent may be improved and an improved thin layer may be obtained through spin-on coating.

Hereinafter, a hardmask composition according to an example embodiment is described.

According to an example embodiment, a hardmask composition including the monomer and a solvent is provided.

The monomer is the same as described above, and one kind of monomer may be used singularly or two or more kinds of monomers may be mixed.

The solvent may be a suitable solvent for sufficiently dissolving or dispersing the monomer and may be, for example at least one selected from propyleneglycol, propyleneglycol diacetate, methoxy propanediol, diethyleneglycol, diethyleneglycol butylether, tri(ethyleneglycol)monomethylether, propyleneglycol monomethylether, propyleneglycol monomethylether acetate, cyclohexanone, ethyllactate, gamma-butyrolactone, methylpyrrolidone, acetylacetone, and ethyl 3-ethoxypropionate.

The monomer may be included in an amount of about 1 to about 50 wt % based on the total amount of the hardmask composition. When the monomer is included in the above range, a desirable thickness of a coated thin layer may be obtained.

The hardmask composition may further include a surfactant.

The surfactant may include, for example, an alkylbenzene sulfonate salt, an alkyl pyridinium salt, polyethylene glycol, or a quaternary ammonium salt, etc.

The surfactant may be included in an amount of about 0.001 to about 3 parts by weight based on 100 parts by weight of the hardmask composition. Within the amount range, the solubility may be secured while maintaining the optical properties of the hardmask composition.

Hereafter, a method for forming patterns by using the hardmask composition is described.

A method of forming a pattern according to an example embodiment includes providing a material layer on a substrate, applying the hardmask composition including the monomer and a solvent on the material layer, heat-treating the hardmask composition to provide a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer using the photoresist pattern to expose a part of the material layer, and etching an exposed part of the material layer.

The substrate may be, for example, a silicon wafer, a glass substrate, or a polymer substrate.

The material layer may be a material to be finally patterned, for example a metal layer such as an aluminum layer, a copper layer, etc., a semiconductor layer such as a silicon layer, etc., or an insulation layer such as a silicon oxide layer, a silicon nitride layer, etc. The material layer may be formed through a method such as a chemical vapor deposition (CVD) process.

The hardmask composition may be applied by spin-on coating in a form of a solution. The hardmask composition may be applied at a thickness of, for example, about 50 Å to about 50,000 Å.

The heat-treating the hardmask composition may be performed at, for example, about 100 to about 500° C. for about 10 seconds to about 10 minutes. During heat-treating, the monomer may cause a self cross-linking and/or mutual cross-linking reaction.

An auxiliary layer may be further formed on the hardmask layer. The auxiliary layer may be a silicon-containing thin layer, and the silicon-containing thin layer may be, for example, silicon nitride or silicon oxide.

A bottom anti-reflective coating (BARC) may be further formed on the silicon-containing thin layer.

Exposure of the photoresist layer may be performed using, for example, ArF, KrF, or EUV. After exposure, heat treatment may be performed at about 100° C. to about 500° C.

The etching process of the exposed part of the material layer may be performed through a dry etching process using an etching gas and the etching gas may be, for example, $CHF_3$, $CF_4$, $Cl_2$, $BCl_3$, or a mixed gas thereof.

The etched material layer may be formed in a plurality of patterns, and the plurality of patterns may be, for example, a metal pattern, a semiconductor pattern, an insulation pattern, or the like, for example, various patterns of a semiconductor integrated circuit device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthesis of Monomer

Synthesis Example 1

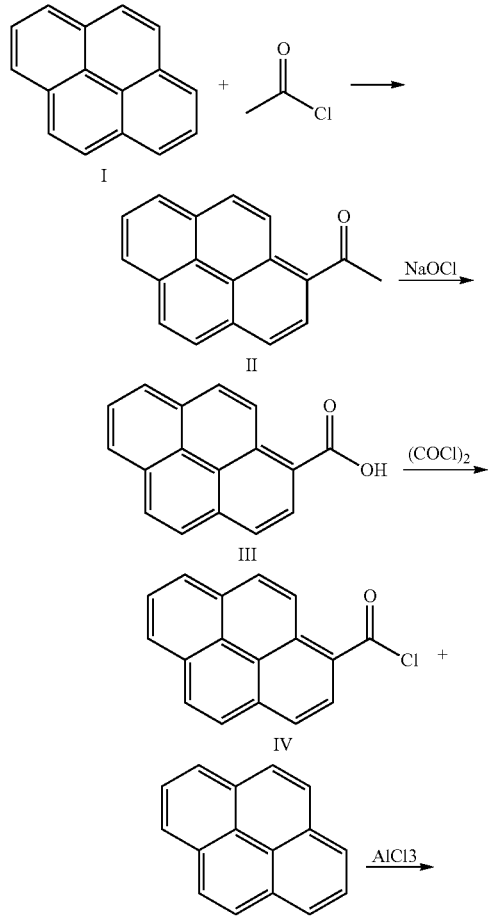

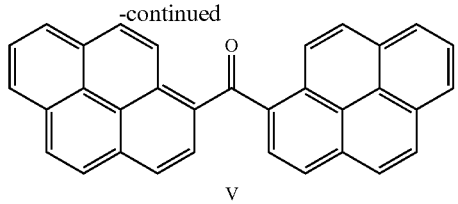

Pyrene (40.5 g, 200 mmol), acetyl chloride (15.7 g, 200 mmol), and dichloroethane (405.0 g) were put in a flask and dissolved. Aluminum chloride ($AlCl_3$, 26.7 g, 200 mmol) was slowly added thereto, and the resultant was agitated at room temperature for 24 hours. When the reaction was complete, the agitated product was cooled down to room temperature, and a potassium hydroxide aqueous solution was added thereto for neutralization. Then, an organic layer produced therein was separated and concentrated, obtaining 48.1 g of a compound (II). A yield of the compound was 98.3%.

The compound II (24.3 g, 100 mmol), sodium hypochlorite (29.8 g, 400 mmol), pyridine (23.7 g, 300 mmol), and dichloroethane (243.3 g) were put in a flask and dissolved. The solution was heated at 80° C. and agitated for 24 hours, and an HCl aqueous solution was added thereto for neutralization. Then, an organic layer was separated and concentrated, obtaining 19.2 g (78.4% of a yield) of a compound (III).

The compound III (24.6 g, 100 mmol), oxalyl chloride (15.23 g, 120 mmol), and DMF (0.08 g, 1 mmol) were added to 246 g of dichloroethane and dissolved therein. The solution was heated at 60° C. and agitated for 12 hours. When the reaction was complete, the agitated solution was cooled down to room temperature. Then, a potassium hydroxide aqueous solution was added to the cooled product for neutralization. Then, an organic layer was separated and concentrated, obtaining 22.7 g of a compound IV (85.8% of a yield).

The compound IV (26.5 g, 100 mmol), pyrene (40.5 g, 200 mmol), and dichloroethane (265 g) were put in a flask and dissolved. Then, aluminum chloride ($AlCl_3$, 26.7 g, 200 mmol) was slowly added to the solution, and the mixture was heated up to 40° C. and agitated for 24 hours. When the reaction was complete, the agitated solution was cooled down to room temperature, and a potassium hydroxide aqueous solution was added thereto for neutralization. Then, an organic layer was separated and concentrated, obtaining 37.6 g (87.2% of a yield) of a compound V.

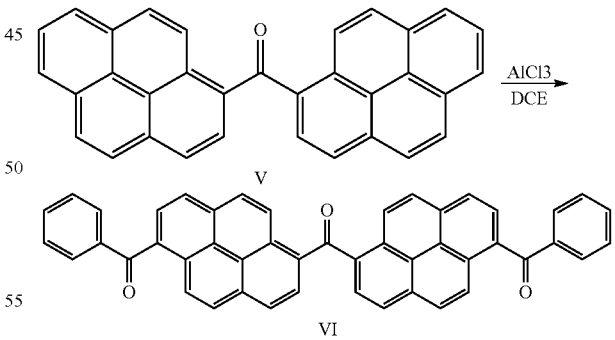

The compound V (43.0 g, 100 mmol) and benzoyl chloride (28 g, 200 mmol) were added to dichloroethane (403 g) in a flask and dissolved therein. Aluminum chloride ($AlCl_3$, 26.7 g, 200 mmol) was slowly added thereto, and the mixture was heated up to 80° C. and agitated for 24 hours.

When the reaction was complete, the agitated solution was cooled down to room temperature, and a potassium hydroxide aqueous solution was added thereto for neutralization. Then, an organic layer was separated and concentrated, obtaining 44.6 g (69.9% of a yield) of a compound VI.

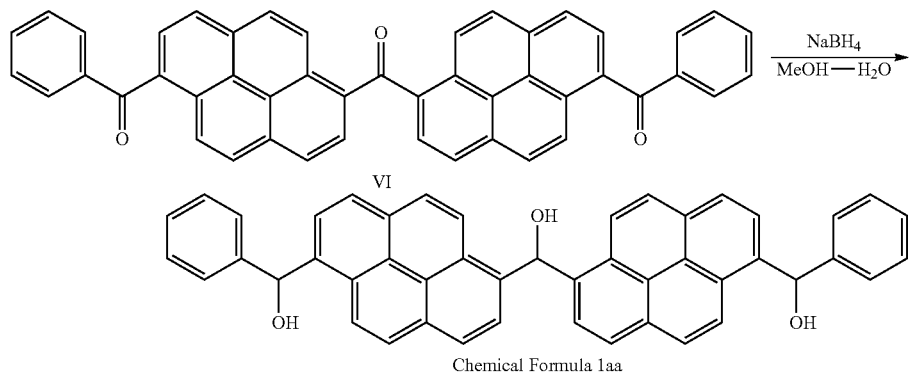

The compound VI (63.9 g, 100 mmol) was dissolved in 639 g of a methanol aqueous solution. Sodium borohydride (38.83 g, 1.0 mol) was slowly added thereto, and the mixture was agitated for 24 hours. When the reaction was complete, a 10% HCl aqueous solution was added to the agitated solution for neutralization, and then, ethyl acetate was added thereto for extraction. Then, an organic layer extracted therein was concentrated under a reduced pressure, obtaining 58.3 g of a compound represented by the following Chemical Formula 1aa. A yield of the compound was 90.4%.

[Chemical Formula 1aa]

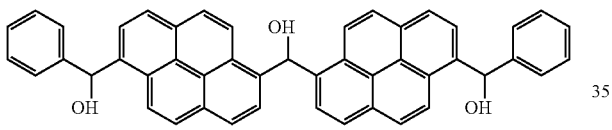

Synthesis Example 2

A compound was synthesized according to the same method as Synthesis Example 1 except for using naphthoyl chloride instead of benzoyl chloride.

The compound was represented by the following Chemical Formula 1bb. A yield of the compound was 79.2%.

[Chemical Formula 1bb]

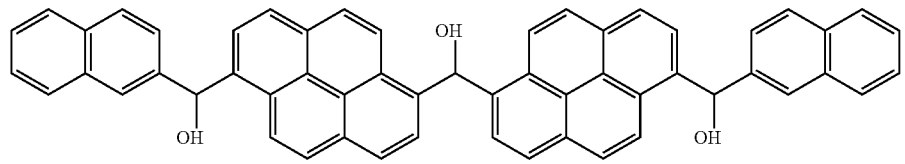

Synthesis Example 3

A compound was synthesized according to the same method as Synthesis Example 1 except for using 4-methoxybenzoyl chloride instead of benzoyl chloride. The compound was represented by the following Chemical Formula 1 cc. A yield of the compound was 87.0%.

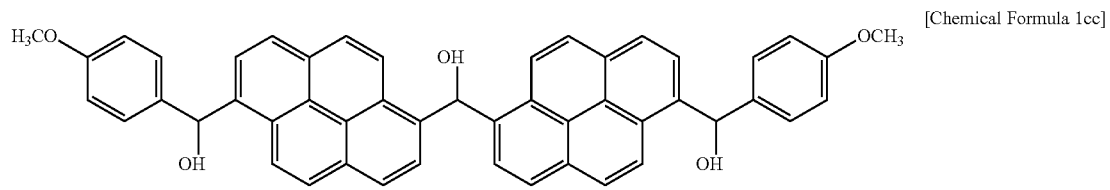 [SMILES: COc1ccc(C(O)c2ccc3ccc4c(C(O)c5ccc6ccc7c(C(O)c8ccc(OC)cc8)ccc8ccc5c6c87)ccc5ccc2c3c54)cc1]

[Chemical Formula 1cc]

Synthesis Example 4

A compound was synthesized according to the same method as Synthesis Example 1 except for using a mixture of benzoyl chloride (100 mmol) and naphthoyl chloride (100 mmol) instead of benzoyl chloride. The compound was represented by the following Chemical Formula 1dd. A yield of the compound was 85.3%.

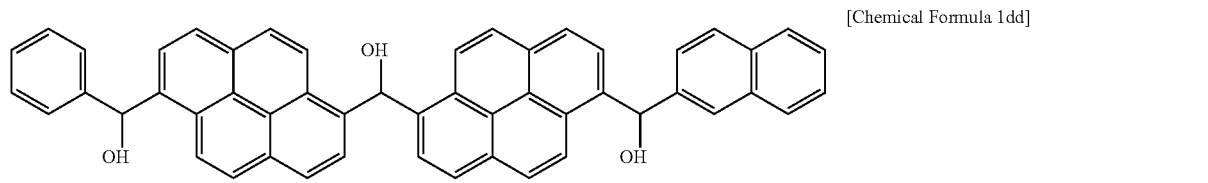 [SMILES: OC(c1ccccc1)c1ccc2ccc3c(C(O)c4ccc5ccc6c(C(O)c7ccc8ccccc8c7)ccc7ccc4c5c76)ccc4ccc1c2c43]

[Chemical Formula 1dd]

Synthesis Example 5

A compound was synthesized according to the same method as Synthesis Example 1 except for using perylene instead of pyrene. The compound was represented by the following Chemical Formula 1ee. A yield of the compound was 77.3%.

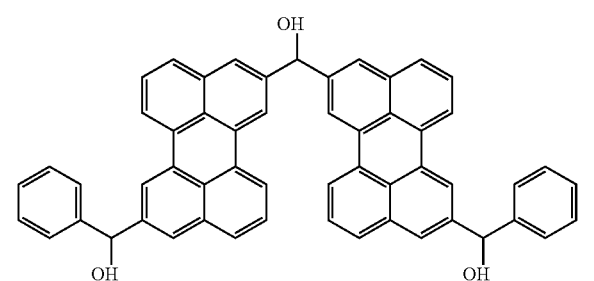

[Chemical Formula 1ee]

Synthesis Example 6

A compound was synthesized according to the same method as Synthesis Example 1 except for using benzoperylene instead of pyrene. The compound was represented by the following Chemical Formula 1ff. A yield of the compound was 71.9%.

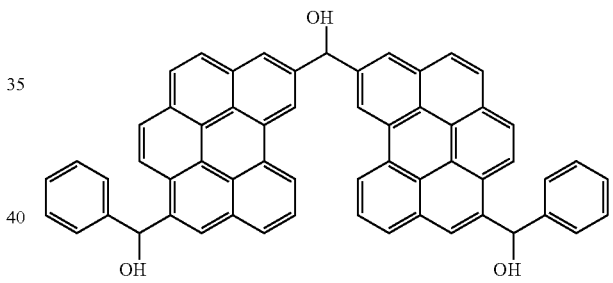

[Chemical Formula 1ff]

Synthesis Example 7

A compound was synthesized according to the same method as Synthesis Example 1 except for using coronene instead of pyrene. The compound was represented by the following Chemical Formula 1gg. A yield of the compound was 65.8%.

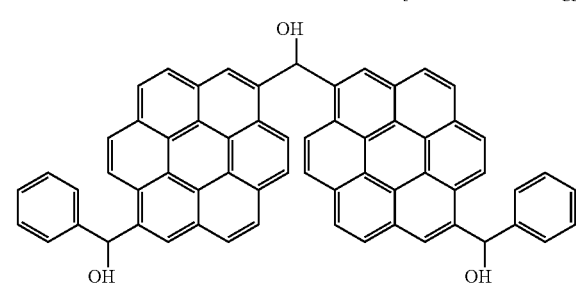

[Chemical Formula 1gg]

Comparative Synthesis Example 1

First Step

Friedel-Crafts Acylation

Pyrene 10.0 g (0.0495 mol), benzoyl chloride 13.9 g (0.0989 mol), and 87 g of 1,2-dichloroethane were put in a flask. 13.2 g (0.0989 mol) of aluminum chloride was slowly added to the solution at room temperature, and the mixture was heated up to 60° C. and agitated for 8 hours. When the reaction was complete, methanol was added to the solution. Then, a precipitate produced therein was filtered, obtaining dibenzoylpyrene.

Second Step

Reduction 5.00 g (0.0122 mol) of dibenzoylpyrene and 57 g of tetrahydrofuran were put in a flask. Next, 4.60 g (0.122 mol) of a sodium borohydride aqueous solution was slowly added to the solution, and the mixture was agitated for 24 hours at room temperature. When the reaction was complete, a 5% hydrogen chloride solution was used to neutralize the agitated reactant to pH 7 and then extracted with ethyl acetate and dried, obtaining a compound represented by the following Chemical Formula 2.

[Chemical Formula 2]

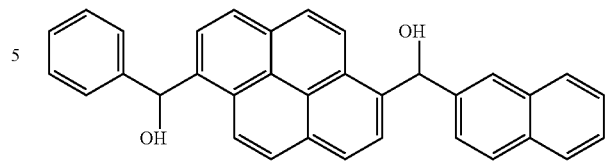

Comparative Synthesis Example 2

A compound was synthesized according to the same method as Comparative Synthesis Example 1 except for using naphthoyl chloride instead of benzoyl chloride. The compound was represented by the following Chemical Formula 3.

[Chemical Formula 3]

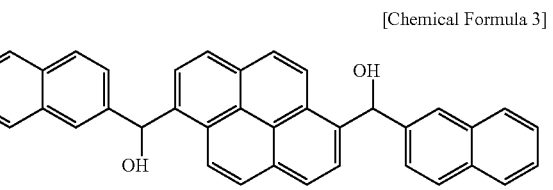

Comparative Synthesis Example 3

A compound was synthesized according to the same method as Comparative Synthesis Example 1 except for using a mixture of benzoyl chloride and naphthoyl chloride instead of benzoyl chloride. The compound was represented by the following Chemical Formula 4.

[Chemical Formula 4]

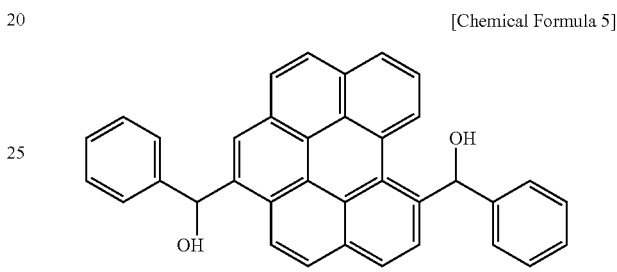

Comparative Synthesis Example 4

A compound was synthesized according to the same method as Comparative Synthesis Example 1 except for using benzoperylene instead of pyrene. The compound was represented by the following Chemical Formula 5.

[Chemical Formula 5]

Preparation of Hardmask Composition

Examples 1 to 7

1 g of each compound of Synthesis Examples 1 to 7 was respectively dissolved in 9 g of propylene glycol monomethylether acetate (PGMEA), and the solution was filtered, preparing hardmask compositions.

Comparative Examples 1 to 4

1 g of each compound according to Comparative Synthesis Examples 1 to 4 was respectively dissolved in 9 g of propylene glycol monomethylether acetate (PGMEA), and the solution was filtered, preparing hardmask compositions.

Evaluation 1: Optical Properties

The hardmask compositions according to Examples 1 to 7 and Comparative Examples 1 to 4 were respectively spin-coated on a silicon wafer and then, baked at 200° C. for 60 seconds to form a 1500 Å-thick hardmask layer. Each hardmask layer was measured regarding refractive index (n) and extinction coefficient (k) by using an ellipsometer (J. A. Woollam Co.).

The results are provided in Table 1.

TABLE 1

| Sample solutions used for manufacturing film | Optical properties (193 nm) | | Optical properties (248 nm) | |
|---|---|---|---|---|
| | Refractive index (n) | Extinction coefficient (k) | Refractive index (n) | Extinction coefficient (k) |
| Example 1 | 1.39 | 0.77 | 2.05 | 0.34 |
| Example 2 | 1.49 | 0.76 | 1.97 | 0.31 |
| Example 3 | 1.50 | 0.69 | 1.99 | 0.35 |

TABLE 1-continued

|  | Optical properties (193 nm) | | Optical properties (248 nm) | |
| --- | --- | --- | --- | --- |
| Sample solutions used for manufacturing film | Refractive index (n) | Extinction coefficient (k) | Refractive index (n) | Extinction coefficient (k) |
| Example 4 | 1.37 | 0.75 | 2.02 | 0.36 |
| Example 5 | 1.45 | 0.73 | 2.01 | 0.33 |
| Example 6 | 1.46 | 0.81 | 1.98 | 0.29 |
| Example 7 | 1.44 | 0.75 | 1.99 | 0.38 |
| Comparative Example 1 | 1.42 | 0.77 | 2.03 | 0.33 |
| Comparative Example 2 | 1.49 | 0.86 | 1.89 | 0.41 |
| Comparative Example 3 | 1.39 | 0.78 | 1.96 | 0.39 |
| Comparative Example 4 | 1.51 | 0.76 | 1.89 | 0.35 |

Referring to Table 1, the hardmask compositions according to Examples 1 to 7 had a refractive index and an absorption degree appropriate for a reflection barrier film at a wavelength of ArF (193 nm) and KrF (248 nm).

Evaluation 2: Etching Selection Ratio

The hardmask layer formed in the Evaluation 1 was dry-etched by $CF_4/CHF_3$ mixed gas. The hardmask layer was measured regarding a thickness difference before/after the etching. The etching conditions are provided in the following Table 2.

TABLE 2

| Chamber pressure | 40.0 Pa |
| --- | --- |
| RF power | 1300 W |
| Gap | 9 nm |
| $CHF_3$ flow | 30 ml/minute |
| $CF_4$ flow | 30 ml/minute |
| Ar gas flow | 100 ml/minute |
| Time | 60 seconds |

The results are provided in the following Table 3.

TABLE 3

| Sample solutions used for manufacturing film | $CF_4/CHF_3$ gas etch rate (nm/minute) |
| --- | --- |
| Example 1 | 43 |
| Example 2 | 42 |
| Example 3 | 39 |
| Example 4 | 41 |
| Example 5 | 37 |
| Example 6 | 35 |
| Example 7 | 32 |
| Comparative Example 1 | 62 |
| Comparative Example 2 | 64 |
| Comparative Example 3 | 59 |
| Comparative Example 4 | 58 |

Referring to Table 3, the hardmask layers formed by coating the hardmask compositions according to Examples 1 to 7 had a low etching rate for $CF_4/CHF_3$ gas and increased an etching selection ratio for a silicon-based hardmask layer.

Evaluation 3: Chemical Resistance

The hardmask compositions according to Examples 1 to 7 and Comparative Examples 1 to 4 were respectively spin-coated on a substrate. The coated substrates were respectively baked to form an about 2800 Å-thick lower layer at a temperature of 200° C., 250° C., 300° C., and 350° C. on a hot plate for 60 seconds. A half of the coated wafer was dipped in a KrF thinner as a peeling solution and taken out, and then measured regarding thickness change before/after dipping using an ellipsometer (J. A. Woollam Co.). In addition, thickness decrease rates at each baking temperature were calculated.

The results are provided in the following Table 4.

TABLE 4

| Thickness decrease (%) | 200° C. | 250° C. | 300° C. | 350° C. |
| --- | --- | --- | --- | --- |
| Example 1 | 21.2 | 11.5 | 0.11 | 0.02 |
| Example 2 | 19.2 | 10.6 | 0.21 | 0.08 |
| Example 3 | 20.1 | 10.7 | 0.22 | 0.09 |
| Example 4 | 18.6 | 11.5 | 0.14 | 0.12 |
| Example 5 | 15.7 | 11.9 | 0.16 | 0.01 |
| Example 6 | 14.3 | 10.0 | 0.14 | 0.04 |
| Example 7 | 11.0 | 9.4 | 0.13 | 0.02 |
| Comparative Example 1 | 26.5 | 17.6 | 0.35 | 0.16 |
| Comparative Example 2 | 33.1 | 16.7 | 0.42 | 0.21 |
| Comparative Example 3 | 27.4 | 14.9 | 0.61 | 0.33 |
| Comparative Example 4 | 26.5 | 16.2 | 0.21 | 0.10 |

Referring to Table 4, the hardmask layers formed of the hardmask compositions according to Examples 1 to 7 had a smaller thickness decrease rate after dipping in a peeling solution than the hardmask layers formed of the hardmask compositions according to Comparative Examples 1 to 4.

By way of summation and review, a method of forming a hardmask layer using spin-on-coating may be used instead of chemical vapor deposition.

The hardmask layer may serve a role of an intermediate layer for transferring a fine pattern of a photoresist to a material layer through a selective etching process. Accordingly, the hardmask layer may desirably exhibit characteristics such as chemical resistance, and etch resistance or the like to be tolerated during the multiple etching processes. Also, resistance for image radiation ray of a short wavelength is desired.

As described above, an embodiment may provide a monomer for a hardmask composition having improved optical properties, etch resistance, and chemical resistance. Another embodiment may provide a hardmask composition including the monomer. Another embodiment may provide a method of forming a pattern using the hardmask composition.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A monomer for a hardmask composition, the monomer being represented by the following Chemical Formula 1:

[Chemical Formula 1]

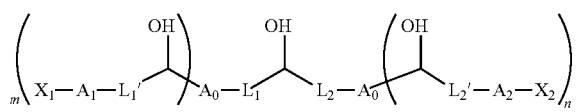

wherein, in the above Chemical Formula 1, $A_0$ is a substituted or unsubstituted polycyclic aromatic group, $A_1$ and $A_2$ are each independently a substituted or unsubstituted C6 to C20 aromatic group, $L_1$, $L_1'$, $L_2$ and $L_2'$ are each independently a single bond or a substituted or unsubstituted C1 to C6 alkylene group, $X_1$ and $X_2$ are each independently hydrogen, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, and m and n are each independently integers of 1 to 6.

2. The monomer as claimed in claim 1, wherein the $A_0$ is selected from the following Group 1:

[Group 1]

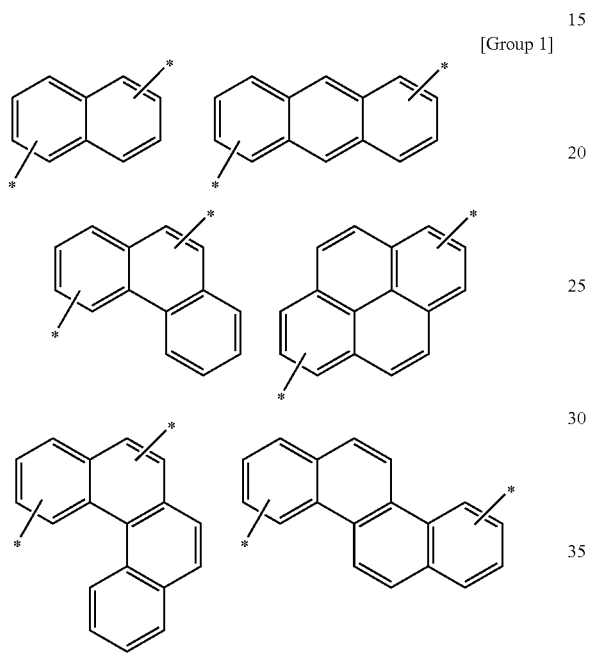

-continued

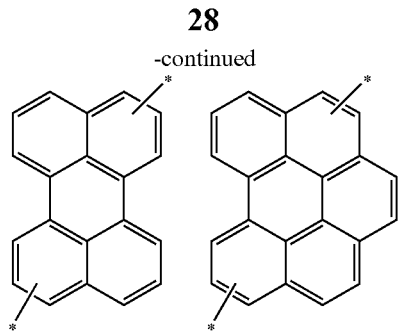

3. The monomer as claimed in claim 1, wherein the $A_1$ and $A_2$ are each independently a substituted or unsubstituted benzyl group, a substituted or unsubstituted naphthyl group, or a substituted or unsubstituted biphenyl group.

4. The monomer as claimed in claim 1, wherein the monomer is represented by one of the following Chemical Formulae 1-1, 1-2, 1-3, 1-4, 1-5, or 1-6:

[Chemical Formula 1-1]

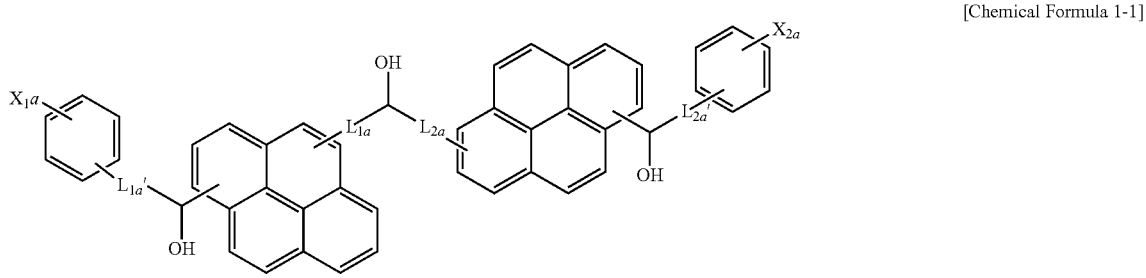

[Chemical Formula 1-2]

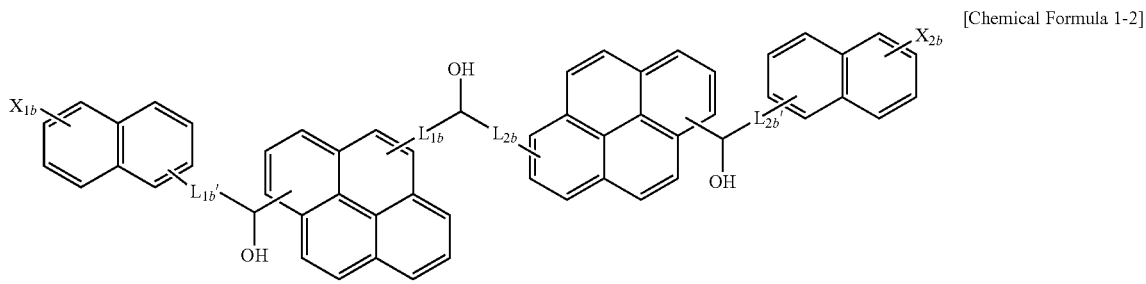

[Chemical Formula 1-3]

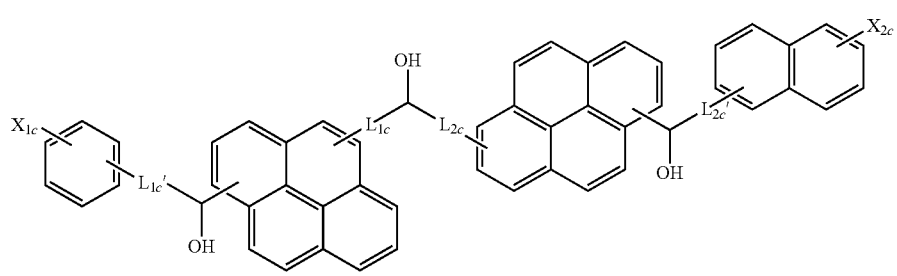

[Chemical Formula 1-4]

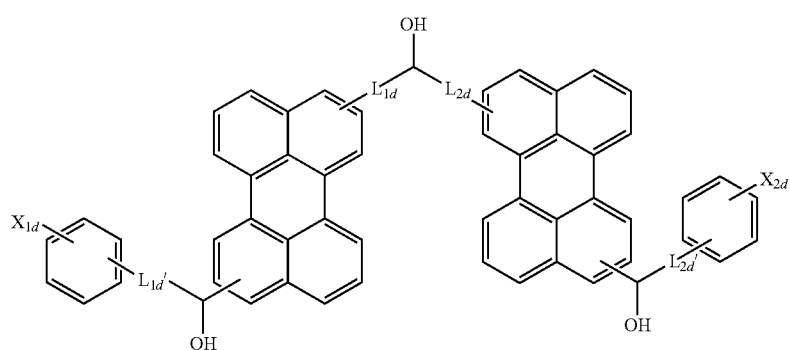

[Chemical Formula 1-5]

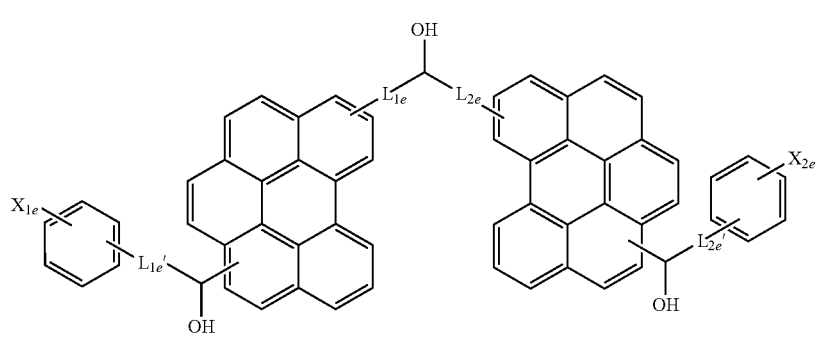

[Chemical Formula 1-6]

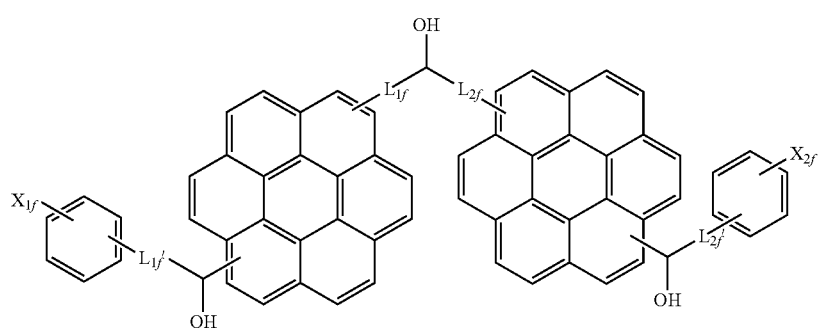

wherein, in the Chemical Formulae 1-1, 1-2, 1-3, 1-4, 1-5, and 1-6, $L_{1a}$, $L_{1b}$, $L_{1c}$, $L_{1d}$, $L_{1e}$, $L_{1f}$, $L_{2a}$, $L_{2b}$, $L_{2c}$, $L_{2d}$, $L_{2e}$, $L_{2f}$, $L_{1a}'$, $L_{1b}'$, $L_{1c}'$, $L_{1d}'$, $L_{1e}'$, $L_{1f}'$, $L_{2a}'$, $L_{2b}'$, $L_{2c}'$, $L_{2d}'$, $L_{2e}'$, and $L_{2f}'$ are each independently a single bond or a substituted or unsubstituted C1 to C6 alkylene group, $X_{1a}$, $X_{1b}$, $X_{1c}$, $X_{1d}$, $X_{1e}$, $X_{1f}$, $X_{2a}$, $X_{2b}$, $X_{2c}$, $X_{2d}$, $X_{2e}$, and $X_{2f}$ are each independently hydrogen, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, and linking positions of each ring are not particularly limited.

5. The monomer as claimed in claim 1, wherein the monomer is represented by one of the following Chemical Formulae 1aa, 1bb, 1cc, 1dd, 1ee, 1ff, or 1gg:

6. The monomer as claimed in claim 1, wherein the monomer has a molecular weight of about 500 to about 5,000.

7. A hardmask composition, comprising:
the monomer as claimed in claim 1, and
a solvent.

8. The hardmask composition as claimed in claim 7, wherein the monomer is included in an amount of about 1 to about 50 wt % based on a total amount of the hardmask composition.

[Chemical Formula 1aa]

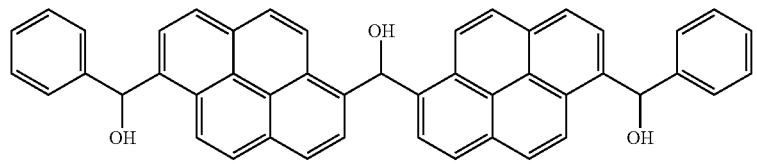

[Chemical Formula 1bb]

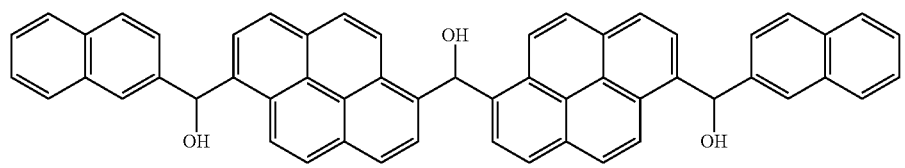

[Chemical Formula 1cc]

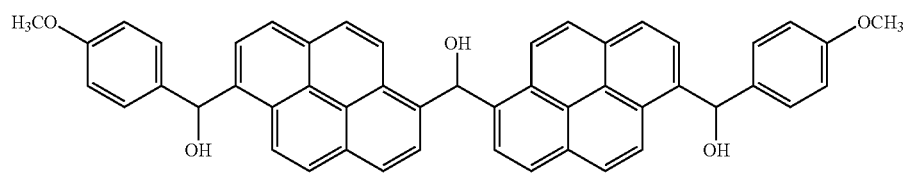

[Chemical Formula 1dd]

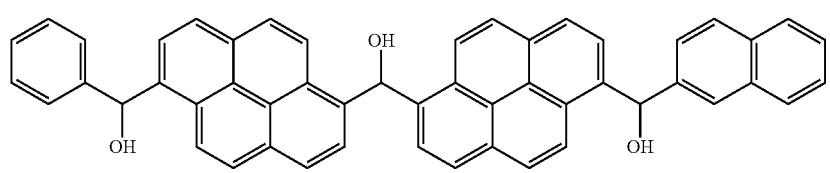

[Chemical Formula 1ee] [Chemical Formula 1ff]

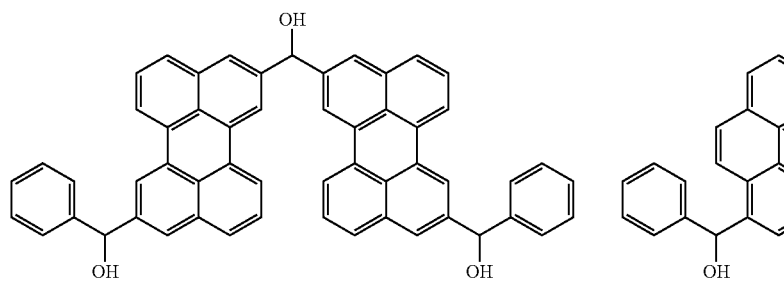
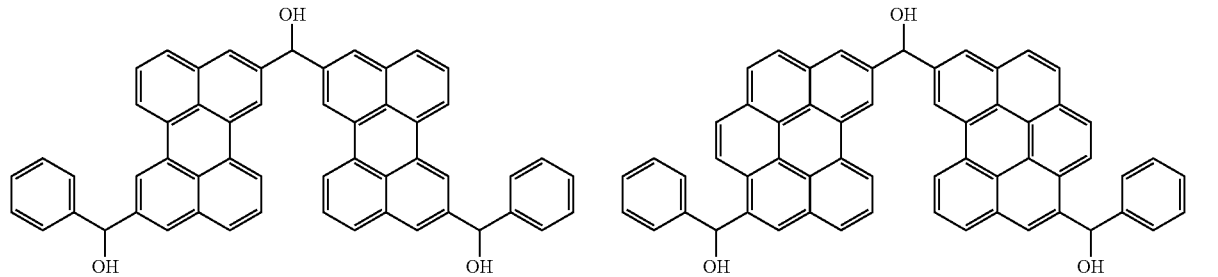

[Chemical Formula 1gg]

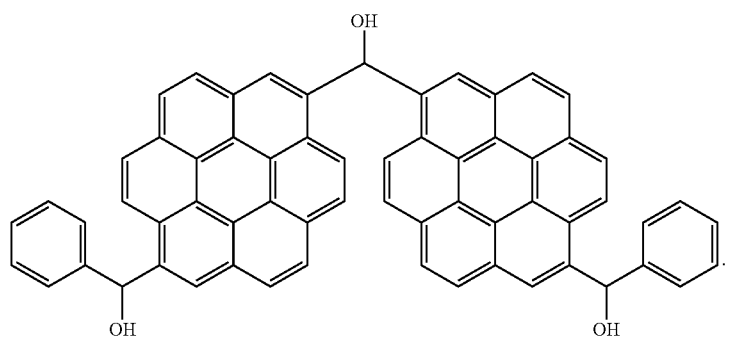

9. A method of forming a pattern; the method comprising:
providing a material layer on a substrate;
applying the hardmask composition as claimed in claim 7 on the material layer;
heat-treating the hardmask composition to provide a hardmask layer;
forming a silicon-containing thin layer on the hardmask layer;
forming a photoresist layer on the silicon-containing thin layer;
exposing and developing the photoresist layer to form a photoresist pattern;
selectively removing the silicon-containing thin layer and the hardmask layer using the photoresist pattern to expose a part of the material layer; and
etching an exposed part of the material layer.

10. The method as claimed in claim 9, wherein the hardmask composition is applied using a spin-on coating method.

11. The method as claimed in claim 9, wherein the hardmask layer is formed by heat-treating the hardmask composition at about 100° C. to about 500° C.

12. A monomer for a hardmask composition, the monomer being represented by one of the following Chemical Formulae 1-1, 1-2, 1-3, 1-4, 1-5, or 1-6:

[Chemical Formula 1-1]

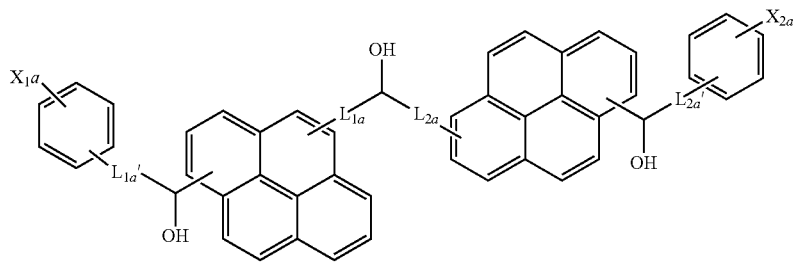

[Chemical Formula 1-2]

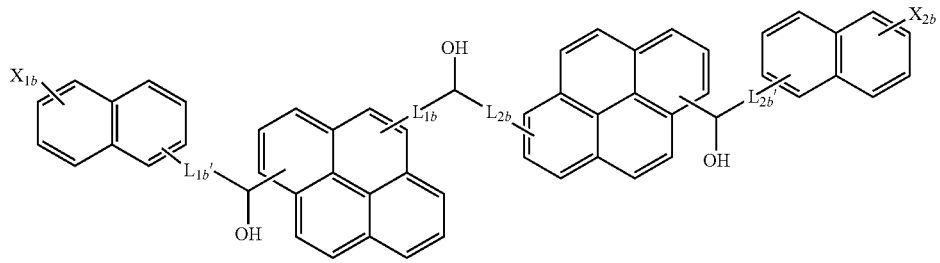

[Chemical Formula 1-3]

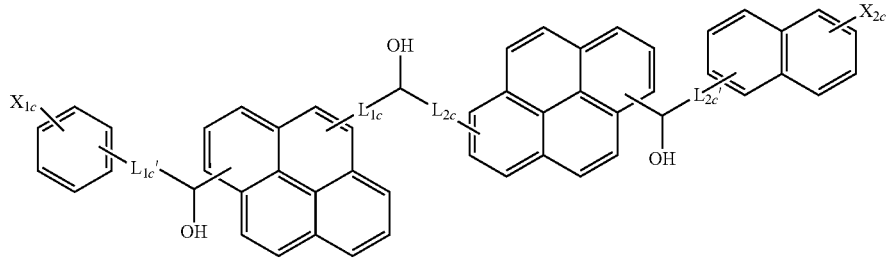

[Chemical Formula 1-4]

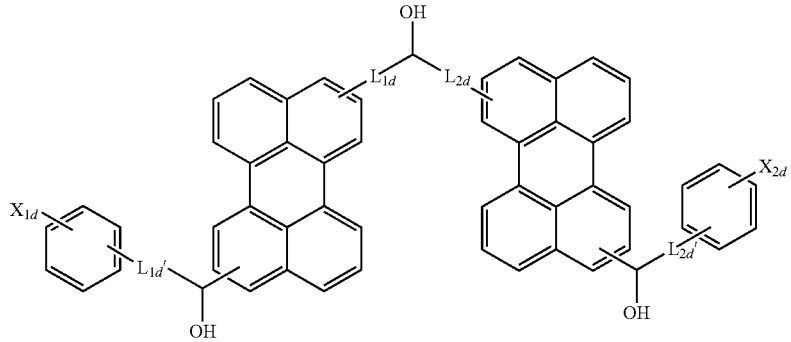

-continued

[Chemical Formula 1-5]

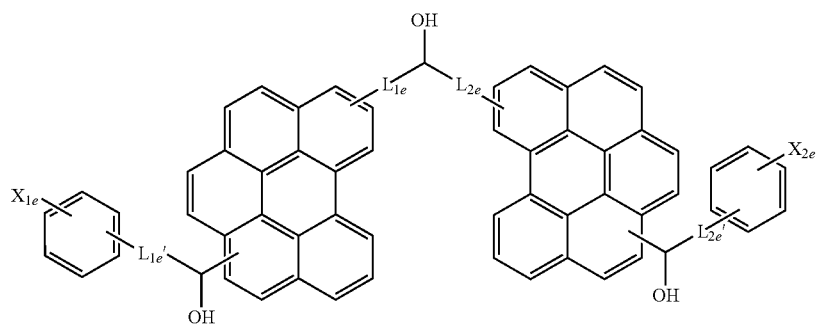

[Chemical Formula 1-6]

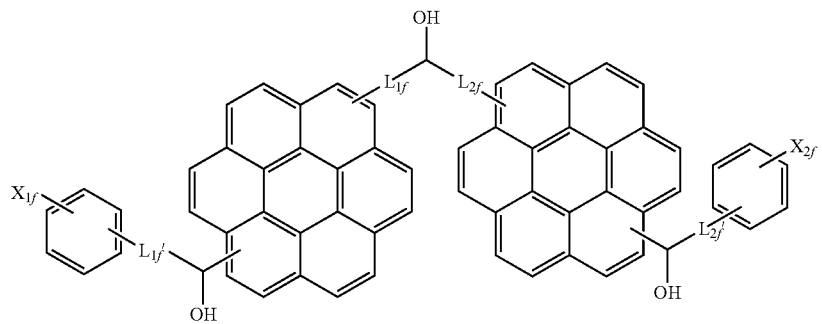

wherein, in the Chemical Formulae 1-1, 1-2, 1-3, 1-4, 1-5, and 1-6, $L_{1a}, L_{1b}, L_{1c}, L_{1d}, L_{1e}, L_{1f}, L_{2a}, L_{2b}, L_{2c}, L_{2d}, L_{2e}, L_{2f}, L_{1a}', L_{1b}', L_{1c}', L_{1d}', L_{1e}', L_{1f}', L_{2a}', L_{2b}', L_{2c}', L_{2d}', L_{2e}',$ and $L_{2f}'$ are each independently a single bond or a substituted or unsubstituted C1 to C6 alkylene group, $X_{1a}, X_{1b}, X_{1c}, X_{1d}, X_{1e}, X_{1f}, X_{2a}, X_{2b}, X_{2c}, X_{2d}, X_{2e},$ and $X_{2f}$ are each independently hydrogen, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, and linking positions of each ring are not particularly limited.

13. The monomer as claimed in claim 12, wherein the monomer has a molecular weight of about 500 to about 5,000.

14. A hardmask composition, comprising:
the monomer as claimed in claim 12, and
a solvent.

15. The hardmask composition as claimed in claim 14, wherein the monomer is included in an amount of about 1 to about 50 wt % based on a total amount of the hardmask composition.

16. A method of forming a pattern; the method comprising:
providing a material layer on a substrate;
applying the hardmask composition as claimed in claim 14 on the material layer;
heat-treating the hardmask composition to provide a hardmask layer;
forming a silicon-containing thin layer on the hardmask layer;
forming a photoresist layer on the silicon-containing thin layer;
exposing and developing the photoresist layer to form a photoresist pattern;
selectively removing the silicon-containing thin layer and the hardmask layer using the photoresist pattern to expose a part of the material layer; and
etching an exposed part of the material layer.

* * * * *